United States Patent
Berg et al.

(10) Patent No.: US 11,583,657 B2
(45) Date of Patent: Feb. 21, 2023

(54) CATHETER SYSTEM

(71) Applicant: Osprey Global, LLC, Cartersville, GA (US)

(72) Inventors: Linda J. Berg, Spring Hill, FL (US); Richard R. Berg, Sr., Spring Hill, FL (US)

(73) Assignee: Osprey Global, LLC, Cartersville, GA (US)

( * ) Notice: Subject to any disclaimer, the term of this patent is extended or adjusted under 35 U.S.C. 154(b) by 676 days.

(21) Appl. No.: 16/519,038

(22) Filed: Jul. 23, 2019

(65) Prior Publication Data

US 2021/0023335 A1 Jan. 28, 2021

(51) Int. Cl.
  *A61M 25/00* (2006.01)
  *A61F 5/44* (2006.01)

(52) U.S. Cl.
  CPC ....... *A61M 25/0017* (2013.01); *A61F 5/4405* (2013.01); *A61F 5/4408* (2013.01); *A61M 25/0075* (2013.01); *A61M 25/0097* (2013.01); *A61M 2210/1085* (2013.01)

(58) Field of Classification Search
  CPC ................ A61F 5/4405; A61F 5/4408; A61M 2210/1085; A61M 25/0017; A61M 25/0075; A61M 25/0097; A61M 2025/024; A61M 2025/0206; A61M 2005/1416; A61M 2025/028
  See application file for complete search history.

(56) References Cited

U.S. PATENT DOCUMENTS

| | | | | |
|---|---|---|---|---|
| 4,139,130 A | * | 2/1979 | Glusker | A45F 3/16 224/660 |
| 4,449,971 A | * | 5/1984 | Cawood | A61F 5/44 604/328 |
| 4,526,298 A | * | 7/1985 | Boxer | A45F 3/16 222/529 |
| 4,665,566 A | * | 5/1987 | Garrow | A61M 25/02 604/179 |
| 4,955,867 A | * | 9/1990 | Endo | A61M 1/285 604/179 |
| 5,496,282 A | * | 3/1996 | Militzer | A61M 25/02 604/179 |
| 5,897,519 A | * | 4/1999 | Shesol | A61M 25/02 602/79 |

(Continued)

FOREIGN PATENT DOCUMENTS

GB 2335344 A * 9/1999 ............ A61M 25/02

OTHER PUBLICATIONS

"Baxter—Secure Way." https://secureway.org/product-category/baxter/accessed Dec. 1, 2022. (Year: 2022).*

(Continued)

*Primary Examiner* — Adam Marcetich
(74) *Attorney, Agent, or Firm* — Baker Donelson Bearman Caldwell & Berkowitz PC

(57) ABSTRACT

A catheter system is disclosed that includes a catheter with an elongated, flexible tube having an entry end, an exit end, and a control valve. The control valve controls the flow of fluids through the catheter tube. The exit end or control valve also includes a coupler which is utilized to allow the catheter to be moved between a stowed condition coupled to a flexible belt and an in-use condition uncoupled from the belt.

9 Claims, 1 Drawing Sheet

(56) References Cited

U.S. PATENT DOCUMENTS

| | | | | |
|---|---|---|---|---|
| 6,032,289 | A * | 3/2000 | Villapiano | A41D 13/1245 2/102 |
| 6,230,513 | B1 * | 5/2001 | Reinmuth | F25D 31/002 222/146.6 |
| 6,439,389 | B1 * | 8/2002 | Mogil | A45F 3/02 206/217 |
| 6,494,344 | B1 * | 12/2002 | Kressel, Sr. | B67D 7/04 222/481.5 |
| 6,544,232 | B1 * | 4/2003 | McDaniel | A61M 25/02 128/DIG. 26 |
| 6,666,360 | B1 * | 12/2003 | Swank | A45F 3/20 224/148.2 |
| 2001/0040190 | A1 * | 11/2001 | Utter | B05B 9/047 239/152 |
| 2005/0035160 | A1 * | 2/2005 | Forsman | A45F 3/14 224/664 |
| 2007/0005031 | A1 * | 1/2007 | Charles | A61F 5/453 604/327 |
| 2007/0187442 | A1 * | 8/2007 | Martin | A01K 29/00 224/148.2 |
| 2010/0121288 | A1 * | 5/2010 | Timmons | A61F 5/4408 604/327 |
| 2011/0180625 | A1 * | 7/2011 | Rotondo | B05B 9/0861 239/152 |
| 2014/0180260 | A1 * | 6/2014 | Mueller | A61M 25/0017 604/544 |
| 2014/0358090 | A1 * | 12/2014 | Wainscott | A61M 25/02 604/179 |
| 2015/0105730 | A1 * | 4/2015 | Alfonso | A61M 25/02 604/179 |
| 2016/0206082 | A1 * | 7/2016 | Gottlieb | B62J 11/16 |
| 2016/0213886 | A1 * | 7/2016 | DiGiorgi | A61M 25/02 |
| 2017/0042724 | A1 * | 2/2017 | Ugarte | A61F 5/4556 |
| 2017/0056630 | A1 * | 3/2017 | Fee | A61M 25/02 |
| 2017/0100276 | A1 * | 4/2017 | Joh | A61F 5/453 |
| 2017/0231804 | A1 | 8/2017 | Miller et al. | |
| 2019/0015636 | A1 * | 1/2019 | Robinson | A61M 25/02 |
| 2019/0133200 | A1 * | 5/2019 | Conner | A41D 27/201 |

OTHER PUBLICATIONS

"Fresenius—Secure Way." https://secureway.org/product-category/fresenius/ accessed Dec. 1, 2022. (Year: 2022).*

* cited by examiner

CATHETER SYSTEM

TECHNICAL FIELD

This invention relates to catheters, and particularly to a catheter system to provide a more natural appearance of use.

BACKGROUND OF THE INVENTION

For different medical reasons, people oftentimes require the use of a catheter which is inserted into the bladder to control and store a person's urine. The Foley type catheter has an elongated tube with two separated channels, or lumens, running down its length. One lumen, open at both ends, drains urine into a collection bag. The other lumen has a valve on the outside end and connects to a balloon the inside tip. The balloon is inflated with sterile water when it lies inside the bladder to stop it from slipping out of the bladder. The external end of the tube is connected to the collection bag which may include a valve to close the tube when changing or emptying the collection bag. The collection bag is typically strapped to the person's leg.

Catheters may also be surgically inserted into the bladder through the abdominal wall, these catheters are sometimes referred to as pubic or suprapubic catheters. Again, these catheters are coupled to an external collection bag which is strapped to the person's leg.

While these catheters collect urine within the collection bag, the bag must be periodically removed and emptied of its contents. The removal of the bag and the disposal of the urine therein may be messy to achieve as well as being embarrassing for the person having the catheter.

A bagless catheter has been devised wherein the catheter may be used without the collection bag, as shown in U.S. Patent Application 2014/0180260. As the external end of the catheter is left to dangle within the wearer's clothing, this catheter may still cause soiling of the wearer's clothing through leakage or drippage.

Another catheter device is shown in U.S. Patent Application Serial Number 2017/0231804. Here a suprapubic catheter is shown which is enclosed within a pouch having a series of catheter supports. The catheter tube must be carefully positioned and accepted into the series of paired supports. Again, this system is complicated to utilize and store: Furthermore, as the catheter must be methodically unlatched and then re-latched into the series of supports located within the pouch, the system does not provide for a natural use and appearance of urination by a wearer. Additionally, the pouch is unsightly and makes it obvious that a catheter is being utilized.

Thus, there has long existed a need for a catheter which enables a person to have a catheter which may be easily utilized for urination in a naturally occurring manner. It is to the provision of such that the present invention is primarily directed.

SUMMARY OF THE INVENTION

A catheter system comprises a catheter having an elongated tube with a first channel extending from an entry end to an exit end, and a control valve coupled to the tube closely adjacent the exit end for controlling the flow of fluids through the tube first channel. The catheter system also includes a flexible belt configured to be worn about the waist of a person, and a coupler releasably mounting the exit end of said tube to the belt in an upright orientation.

DETAILED DESCRIPTION

Figure 1:
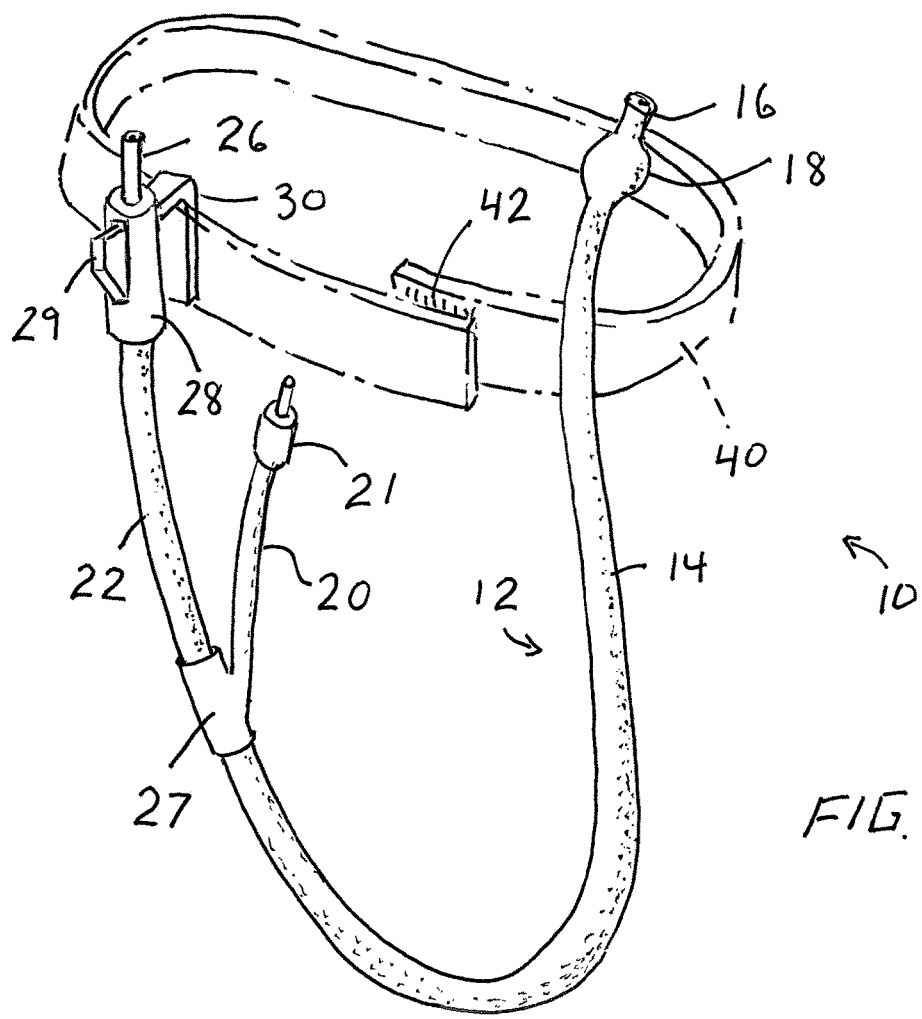
FIG. 1 is a catheter system in a preferred form of the invention.

With reference next to the drawings, there is shown a catheter system 10 of the present invention in a preferred form. The catheter system 10 includes a conventional bagless catheter 12. The bagless catheter mimics normal bladder function by using a patient's bladder to store urine. Furthermore, the bagless catheter helps a patient maintain normal bladder function during the period of catheterization. However, the present invention may include any type of catheter, including, but not limited to, suprapubic or pubic catheters.

The catheter 12 has an elongated, flexible tube 14 having an internal or entry end 16 which is inserted through a patient's urethra into the patient's bladder or surgically inserted int the patient's bladder through the abdominal wall (pubic catheter). The internal end 16 includes an inflatable balloon 18 which has a deflated condition for insertion and an inflated condition for use.

The exposed portion of the catheter 12 outside the patient's body includes a first channel or lumen 20 which has a balloon port 21 which controls inflation of the balloon 18 coupled to the internal end 16 of the tube 14. The exposed portion of the catheter 12 also includes a second channel or lumen 22 which has an open, terminal, or exit end 26 and a control valve 28 directly adjacent the exit end 26. The second channel 22 extends to the channel opening at the internal end 16. The control valve 28 may be any type of valve, such as an inline ball valve or an external pinch type valve, which controls the flow of fluids through the second channel 22. The first and second channels 20 and 22 are joined to a connection 27 wherein they continue together to become the internal end 16.

The control valve 28 has a spring biased control button or lever 29, which when depressed allows the flow of fluids through the control valve 28 to the terminal end 26, the spring biasing returning the lever to its original, closed position preventing the flow of fluids through the catheter. The terminal end 26 or control valve 28 also includes a coupler 30, shown in the form of a generally U-shaped mounting clip in FIG. 1. The coupler 30 is utilized to allow the catheter to be moved between a stowed condition coupled to a later described belt and an in-use condition uncoupled from the belt.

The catheter system 10 also includes a flexible strap, harness or belt 40 configured to fit about the waist of a patient. The belt 40 includes a buckle or other fastener 42 to allow adjustable fitting of the belt 40 for various waist sizes. The fastener 42 may be any type of conventional fastener, such as hook and loop type fastener designed to mesh or interlock, a snap, button, or other device. The coupler 30 is utilized to allow the catheter to be moved between a stowed condition coupled to the belt in an upright orientation and an in-use condition uncoupled from the belt.

In use, the catheter 12 is inserted into the bladder with the balloon 18 in a retracted or deflated condition. The balloon 18 is then inflated to prevent the catheter internal end 16 from accidentally slipping out of the bladder. To inflate the balloon 18, a syringe filled with sterile water is coupled to the balloon port 21 and the sterile water is injected to pressurize and expand the balloon 18.

When the patient wants to drain urine from his or her bladder, the patient simply opens, moves, or removes an article of clothing to gain access to the terminal end 26 of the catheter 12 and in the same manner as in a normal urination process. The terminal end 26 is then released from the belt 40 through the disconnecting of the clip 30 from the belt 40 and the terminal end 26 is manually lowered to position or aim fluids exiting the terminal end in a direction into a toilet, urinal, bedpan or other waste receptacle, again providing the appearance of the normal urination process.

The person then opens the control valve 28 through the depression or actuation of the control valve level 29 to allow the flow of urine from the bladder through the second channel 22 from the internal end 16 within the bladder to the terminal end 26. Thus, the person has easy access to the catheter terminal end 26 and the control of urine from the bladder in an easy manner which also has a natural outward appearance so as not to be conspicuous or obvious to others.

Once the urination process is complete, the person may then re-couple the mounting clip or coupler 30 to the belt 40 and returns the clothing to their initial position. The near vertical or upright orientation of the terminal end 26 and immediately adjacent portion of the tube 14 restricts any dripping of fluids from the catheter. The simple coupling of the terminal end 26 to the belt 40 also allows for a quick, efficient and un-noticeable stowing of the catheter.

It should be understood, that the mounting clip 30 may be coupled to the patients waistband of his or her pants, underwear or other article of clothing in an upright orientation as an alternative to coupling to the additional belt 40. Thus, the belt 40 may be eliminated if such mounting to clothing is available and desired.

Figure 2:
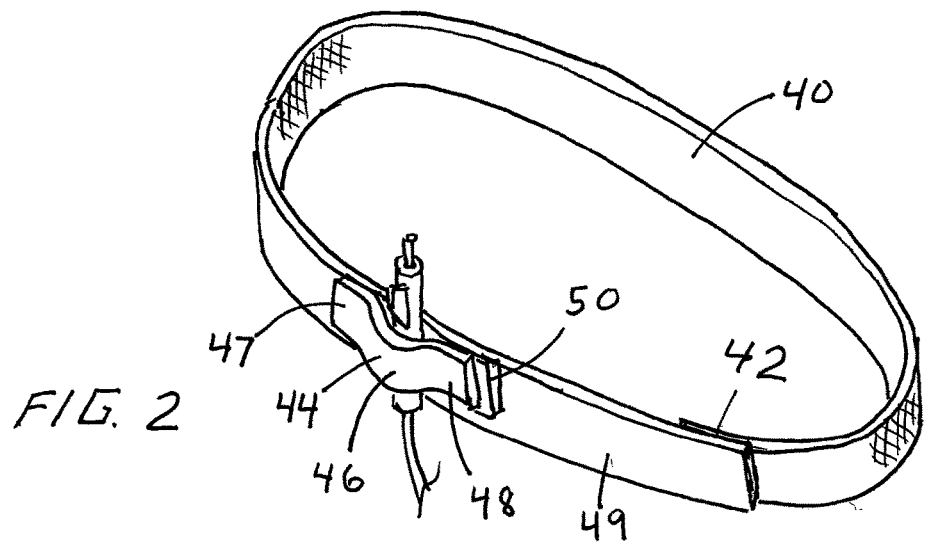
FIG. 2 is a catheter system in another preferred form of the invention.

With reference next to FIG. 2, there is shown a catheter system 50 in another preferred form of the invention. The catheter system 50 is essentially the same as that previously described except for the coupling of the terminal end 26 to the belt 40.

Here, the belt 40 includes a coupler 44 in the form of a releasable strip, loop, or strap 46 having a fixed end 47 and an oppositely disposed releasable free end 48 which is releasably coupled to a main portion 49 of the belt 40. The strap 46 may include any type of conventionally know releasable fastener 50, such as a snap or the hook and loop type fastener shown in the drawing. The combination of the strap 46 and fastener 50 may be considered to be a fastener or coupler.

In use, the patient simply moves his or her clothing to gain access to the terminal end 26 and strap 46. The free end 47 of the strap 46 is then released from the main portion 49 of the belt 40 and the catheter 12 is utilized as previously discussed.

It thus is seen that a catheter system is now provided which allows quick and easy access to the catheter for a natural appearance during the process of emptying one's bladder. Indeed, while the catheter system has been shown and described in its preferred forms, many changes, additions and deletions may be made thereto without departure from the spirit and scope of the invention as set forth in the following claims.

The invention claimed is:

1. A catheter system comprising,
a catheter having an elongated tube with a first channel extending from an entry end to an exit end, and a control valve coupled to said tube closely adjacent said exit end for controlling the flow of fluids through said tube first channel;
a flexible belt configured to be worn about the waist of a person, and
a coupler fixed ly mounted to said elongated tube at a location adjacent said exit end releasably mounting said exit end of said tube to said belt, said coupler being configured to orient said tube exit end in an upright orientation when coupled to said belt.

2. The catheter system of claim 1 wherein said coupler is a mounting clip.

3. The catheter system of claim 2 wherein said mounting clip is coupled to said control valve.

4. The catheter system of claim 1 wherein said catheter includes an inflatable balloon, a balloon port, and a second channel extending from said balloon port to said inflatable balloon.

5. A catheter system comprising,
a catheter having an elongated tube extending from an entry end to an exit end, and a control valve coupled to said tube for controlling the flow of fluids through said tube;
a flexible belt configured to be worn about the waist of a person, and
a fastener mounted to said elongated tube at a location adjacent said exit end coupling said catheter exit end to said flexible belt for movement between a stowed condition wherein said catheter is coupled to said belt and an in-use condition wherein said catheter is uncoupled from said belt.

6. The catheter system of claim 5 wherein said fastener is a mounting clip.

7. The catheter system of claim 6 wherein said mounting clip is coupled to said control valve.

8. The catheter system of claim 5 wherein said catheter includes an inflatable balloon, a balloon port, and a balloon channel extending from said balloon port to said inflatable balloon.

9. The catheter system of claim 5 wherein said fastener couples said catheter exit in an upright orientation to said flexible belt.

* * * * *